(12) United States Patent
Schenk

(10) Patent No.: US 9,011,327 B2
(45) Date of Patent: Apr. 21, 2015

(54) CAPACITIVE SENSING AND COMMUNICATING

(75) Inventor: Tim Corneel Wilhelmus Schenk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 604 days.

(21) Appl. No.: 12/809,229

(22) PCT Filed: Dec. 18, 2008

(86) PCT No.: PCT/IB2008/055422
§ 371 (c)(1),
(2), (4) Date: Jun. 18, 2010

(87) PCT Pub. No.: WO2009/081348
PCT Pub. Date: Jul. 2, 2009

(65) Prior Publication Data
US 2010/0312071 A1    Dec. 9, 2010

(30) Foreign Application Priority Data

Dec. 20, 2007 (EP) ..................................... 07123791

(51) Int. Cl.
*A61B 5/00* (2006.01)
*H04W 74/08* (2009.01)
(Continued)

(52) U.S. Cl.
CPC ....... *H04B 13/005* (2013.01); *A61B 2562/0214* (2013.01); *A61B 5/0002* (2013.01);
(Continued)

(58) Field of Classification Search
CPC ...... A61B 5/0028; A61B 5/0002; A61B 5/68; A61B 5/6801; H04B 13/005; H04B 7/2643; H04B 7/2671; G06F 19/34; G06F 19/3418; H04W 84/005; H04W 74/0891
USPC ................. 600/300–301, 363–365, 372–374, 600/377–379, 382–384, 386–394, 481, 485, 600/500–503, 508, 515–519, 529–531, 600/544–547, 549, 587–595; 128/920–925; 705/2–3
See application file for complete search history.

(56) References Cited

U.S. PATENT DOCUMENTS 3,742,937 A * 7/1973 Manuel et al. ................ 600/503
4,784,162 A * 11/1988 Ricks et al. ................... 600/484
(Continued)

FOREIGN PATENT DOCUMENTS

| EP | 1821432 A1 | 8/2007 |
| WO | 2006064397 A2 | 6/2006 |
| WO | 2007096810 A1 | 8/2007 |

OTHER PUBLICATIONS

Zimmerman, T. G. "Personal Area Networks: Near field intrabody communication", IBM Systems Journal, vol. 35, No. 3&4, 1996, p. 609-617.*

(Continued)

*Primary Examiner* — William Thomson
*Assistant Examiner* — Marie Archer

(57) ABSTRACT

The invention relates to a device being placeable on or close to a human or animal body, wherein the device comprises a sensing unit configured to capacitively sense a physiological signal from the human or animal body and capacitively communicate a body coupled communication signal for a body area network (BAN). With the device a single sensing unit can be used to sense or measure a physiological signal and communicate a body coupled communication signal. Advantageously, the same couplers can simultaneously be used for sensing, transmitting and receiving. The device does not require an extra antenna and RF unit and there is no need for using wires.

16 Claims, 5 Drawing Sheets

(51) Int. Cl.
  H04B 7/26 (2006.01)
  H04B 5/00 (2006.01)
  G06F 19/00 (2011.01)
  H04B 13/00 (2006.01)
  H04B 7/00 (2006.01)
  H04W 84/00 (2009.01)
  H04W 74/00 (2009.01)
  A61B 5/0402 (2006.01)
  A61B 5/0476 (2006.01)
  A61B 5/0488 (2006.01)

(52) U.S. Cl.
  CPC .............. *A61B 5/72* (2013.01); *A61B 5/6801* (2013.01); *H04W 74/0891* (2013.01); *H04W 84/005* (2013.01); *G06F 19/3418* (2013.01); *H04B 7/2671* (2013.01); *A61B 5/0006* (2013.01); *A61B 5/0024* (2013.01); *A61B 5/0028* (2013.01); *A61B 5/0402* (2013.01); *A61B 5/0476* (2013.01); *A61B 5/0488* (2013.01); *G06F 19/3406* (2013.01); *H04B 5/0012* (2013.01)

(56) References Cited

U.S. PATENT DOCUMENTS

| | | | | |
|---|---|---|---|---|
| 5,208,809 | A * | 5/1993 | Fergeson et al. | 370/545 |
| 5,738,104 | A * | 4/1998 | Lo et al. | 600/521 |
| 5,914,701 | A | 6/1999 | Gersheneld et al. | |
| 7,447,526 | B2 * | 11/2008 | Kim et al. | 455/574 |
| 7,935,061 | B1 * | 5/2011 | Breed et al. | 600/485 |
| 2003/0092973 | A1 * | 5/2003 | Kim et al. | 600/300 |
| 2003/0144581 | A1 * | 7/2003 | Conn et al. | 600/309 |
| 2004/0062133 | A1 * | 4/2004 | Tsuji | 365/232 |
| 2004/0204744 | A1 * | 10/2004 | Penner et al. | 607/23 |
| 2006/0047987 | A1 * | 3/2006 | Prabhakaran et al. | 713/322 |
| 2006/0136015 | A1 | 6/2006 | Park et al. | |
| 2007/0190940 | A1 | 8/2007 | Lee et al. | |
| 2007/0244370 | A1 * | 10/2007 | Kuo et al. | 600/300 |
| 2008/0076974 | A1 * | 3/2008 | Yamazaki et al. | 600/300 |
| 2008/0139953 | A1 * | 6/2008 | Baker et al. | 600/509 |
| 2008/0143512 | A1 * | 6/2008 | Wakisaka et al. | 340/504 |
| 2008/0214946 | A1 * | 9/2008 | Miller et al. | 600/516 |
| 2008/0262376 | A1 * | 10/2008 | Price | 600/547 |
| 2008/0287813 | A1 * | 11/2008 | Kirstein et al. | 600/488 |
| 2010/0323634 | A1 * | 12/2010 | Kimura | 455/68 |

OTHER PUBLICATIONS

Zimmerman, T. G, "Personal Area Networks (PAN): Near-Field Intra-Body Communication", Master of Science in Media Arts and Sciences at the Massachusetts Institute of Technology, Sep. 1995, p. 1-81.*

Lee, J. M. "Evaluation of a Capacitively-Coupled, Non-Contact (through Clothing) Electrode or ECG Monitoring and Life Signs Detection for the Objective Force Warfighter", Walter Reed Army Institute of Research (WRAIR), Paper presented at the RTO HFM Symposium on Combat Casualty Care in Ground Based Tactical Situations: Trauma Technology and Emerge.*

Baxter, L. K. in "Capacitive Sensors"; copyright Jun. 26, 2000, revised Jul. 20, 2000; pp. 1-17 teaches fundamental aspects of parallel plate capacitor design considerations.*

Chen, Z. et al; "Self Organization and Energy Efficient TDMA MAC Protocol by Wake Up for Wireless Sensor Networks"; Sensor and Ad Hoc Communications and Networks2004, IEEE. SECON. 2004, p. 335-341.*

Akyldiz, I. F. et al; "Wireless Multemedia Sensor Networks: A survey". IEEE Wireless Communications. Dec. 2007, p. 32-39.*

Arisha, K. et al. in "System-Level Power Optimization for wireless Multimedia Communication". Editors: Ramesh, K and Goodman, D.; Springer US; 2002, p. 21-40.*

Cardei, M. et al; "Improving Wireless Sensor Network Lifetime through Power Aware Organization"; Wireless Networks 11, 333-340, 2005.*

Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004, Springer-Verlag Berlin Heidelberg 2004.*

Holt, B. et al. "Flexible Power Scheduling for Sensor Networks", IPSN'04, Apr. 26-27, 2004, Berkeley, California, USA. p. 1-10.*

Lee, W. L; "Flexible-Schedule-Based TDMA Protocols for Supporting Fault-Tolerance, On-Demand TDMA Slot Transfer, and Peer-to-Peer Communication in Wireless Sensor Networks"; Thesis for the degree of Doctor in Philosophy, University of Western Australia, 2007, p. 1-213.*

Sohrabi, K. et al; "Protocols for Self-Organization of a Wireless Sensor Network", IEEE Personal Communications; Oct. 2000, p. 16-27.*

Sivrikaya, F. et al; "Time synchronization in Sensor Networks: A Survey"; IEEE Network, Jul./Aug. 2004, p. 45-50.*

* cited by examiner

CAPACITIVE SENSING AND COMMUNICATING

FIELD OF THE INVENTION

The present invention generally relates to a device, a system, a method and a computer program for sensing a physiological signal and communicating a body coupled communication (BCC) signal.

BACKGROUND OF THE INVENTION

Body area networks (BANs) are a subset of wireless personal area networks (WPANs), which in turn are a subset of personal area networks (PANs). Such networks can be used for communicating data between devices that are located close to one person.

BCC has been proposed as a prime candidate for the physical layer technology of BANs. It is also considered in the IEEE 802.15.6 BAN standardization.

BCC signals are conveyed over a human body instead of through the air. Therefore, a communication based on such signals is confined to an area close to the human body. This is in contrast to radio frequency (RF) communications, where a much larger area is covered.

Thus, when using BCC signals, a communication is only possible between devices situated on, connected to or placed close to the same human body. This enables the creation of a secure BAN.

A schematic diagram of a BCC system is shown in FIG. 7. A BCC system 700 comprises a transmitter 705 and a receiver 710 as well as electrodes 715, 720, 725 and 730. The transmitter 705 is connected to the electrodes 715 and 720, and the receiver 710 is connected to the electrodes 725 and 730, wherein each of the electrodes 715, 720, 725 and 730 is illustrated as a flat plate in FIG. 7. The transmitter 705 is capacitively coupled to the receiver 710 through a human body in order to transmit signals from the former to the latter. For example, they can be capacitively coupled through a person's forearm as depicted in FIG. 7. As an electrostatic coupling is used to transmit signals from the transmitter 705 to the receiver 710, a current return path is required. Such return path is provided by the air (dielectric) and earth ground (dielectric and conductor).

BAN technology may be applied in medical on-body sensor networks, where it is important that the sensors exchange data (or identification keys) only with other sensors on the same human body. Other applications of this technology can be e.g. in the fields of sports, military and security.

On the other hand, capacitive technology has also been proposed for sensing physiological signals such as e.g. electrocardiogram (ECG) signals, electroencephalogram (EEG) signals and electromyogram (EMG) signals. When using capacitive technology, the sensing can be contactless. That is, a sensor does not have to touch a person's body. This is in contrast to previously proposed sensor systems such as e.g. a usual ECG system. With these systems the sensors have to be glued or connected with gel to a person's body. As no such contact is needed when using capacitive technology, sensors may be integrated e.g. in clothing with this technology. Thus, new applications such as e.g. in the field of wellness are enabled by employing capacitive technology for sensing purposes.

A schematic diagram of a capacitive physiological sensing device is shown in FIG. 8. A capacitive physiological sensing device 800 comprises a sensor processing unit 805 as well as electrodes 810 and 815. The sensor processing unit 805 is connected to the electrodes 810 and 815. The electrodes 810 and 815 are placed close to a human body in order to pick up a signal from the same by means of a capacitive coupling. As illustrated in FIG. 8, they may be located e.g. at a person's forearm. A raw signal picked up by the electrodes 810 and 815 is input to the sensor processing unit 805, which conditions and processes this raw signal to obtain a desired physiological signal such as e.g. an ECG signal.

Physiological signals output by capacitive physiological sensing devices such as e.g. the capacitive physiological sensing device 800 shown in FIG. 8 can be transmitted over wires or via RF technology (such as e.g. ZigBee or WiFi). If the physiological signals are transmitted over wires, all capacitive physiological sensing devices have to be connected by wires. This may result in many errors during operation of a system comprising a plurality of capacitive physiological sensing devices. For example, when using such system in a clinical environment, errors may occur due to loose contacts and people moving. Further, a system of this kind does not provide a convenient sensing for lifestyle applications such as e.g. wellness and sports, due to a clutter of wires. In summary, sensing systems based on wired communications are unreliable and inconvenient.

The above mentioned problems can be solved by using RF connections or links for transmitting physiological signals. However, such RF links show the disadvantage that a human body at which sensing devices for sensing the physiological signals are located blocks the RF links. Further, the RF communication range is not limited to one person. An additional disadvantage of the RF approach consists in that an extra RF communication solution has to be added to every sensing device, which significantly increases the costs of the solution and its power consumption.

Thus, the operation of RF-based sensing systems becomes unreliable due to body blockage. Further, their operation even becomes insecure due to providing a communication range that is not limited or restricted to one person. In addition, each sensing device of such system requires an extra antenna and RF solution for the communication.

WO 2006/064397 A2 discloses a wireless network for monitoring a patient, wherein the wireless network comprises at least one wearable monitor including a physiological condition sensor coupled to the patient to sense data related to one physiological function of the patient, and a first body communication unit that interfaces with the physiological condition sensor to communicate over the patient utilizing a near field capacitive body coupled protocol. The wireless network further comprises a relay system including a second body communication unit that receives data from and communicates with the first body communication unit utilizing the near field capacitive body coupled protocol, and an external communication unit that communicates the data to a remote medical monitoring station. That is, the arrangement described in this document comprises a conventional sensor dedicated to sensing purposes and a separate body communication unit dedicated to communicating purposes.

SUMMARY OF THE INVENTION

It is desirable to have a reduced number of devices. It is further desirable to reduce the size, the complexity and the costs of the arrangement. It is still further desirable to decrease the power consumption of this arrangement as compared to using separate sensor and communication units.

Such desires are fulfilled by a device according to claim 1 and a method according to claim 19.

Accordingly, in a first aspect of the present invention a device being placeable on or close to a human or animal body is presented, wherein the device comprises a sensing unit configured to capacitively sense a physiological signal from the human or animal body and capacitively communicate a body coupled communication signal for a body area network. That is, a capacitive sensing device with body coupled communication capabilities is provided. With the device a single sensing unit can be used to sense or measure a physiological signal and communicate a body coupled communication signal. In other words, the same couplers can simultaneously be used for sensing, transmitting and receiving. Thus, sensing and communicating can be performed at the same time by the same sensing unit. Hence, the size, the costs and the power consumption of the device can be reduced in comparison with those of previously proposed devices. The device may potentially be ultra low-power and low-cost, since it does not require an extra antenna and RF unit. Moreover, there is no need for using wires. Therefore, no clutter of wires occurs with the device.

The device according to the first aspect can comprise a first filtering unit configured to low-pass filter or band-pass filter the physiological signal. The first filtering unit enables to remove other spectral content not belonging to the sensed physiological signal. For example, communication signals from other devices may be filtered out so as to obtain a relevant physiological signal content free from any artefacts. Thus, an improved measurement of a desired physiological quantity can be achieved.

The device can also comprise a processing unit configured to process a signal based on the physiological signal. The processing unit may retrieve the desired physiological quantity to be sensed. That is, it can condition and process a raw signal picked up by the sensing unit to get the physiological quantity. Thereby, an exact value of the physiological quantity can be obtained.

The device may comprise a second filtering unit configured to high-pass filter or band-pass filter a received body coupled communication signal. Utilizing the second filtering unit, physiological signal content and any high frequency noise can be removed. Thereby, an improved communication with a reduced error rate can be provided.

The device can comprise a detecting unit configured to detect data conveyed by a received body coupled communication signal. The detecting unit enables to retrieve data transmitted from another device, e.g. physiological data sensed by the other device. Thus, data transmitted by another device can be retrieved while at the same time gaining local physiological data by means of the sensing unit.

The device may comprise a storing unit configured to store at least one of data based on the physiological signal, data conveyed by a received body coupled communication signal and data conveyed by another communication signal. Storing data allows for further processing of the same. For example, a data fusion can be applied so as to obtain a more accurate estimate of a physiological quantity.

The device can comprise a combining unit configured to combine at least one of a plurality of data generated by the device at different points in time and a plurality of data generated by different devices. The combining unit may be used to combine different measured data in order to make some decision or to derive another estimate of a physiological quantity that may be more accurate than an estimate achievable by using a single data, for example by combining data generated by different devices so as to decrease the impact of motion artefacts occurring with capacitive sensing.

The device can comprise a transmit data generating unit configured to generate transmit data from at least one of stored data and combined data, and other data. By using the transmit data generating unit it is possible to generate compact transmit data blocks that can include a plurality of physiological data and other data. Thereby, an efficient transmission of data may be performed.

The device can comprise a modulating unit configured to modulate transmit data to obtain a body coupled communication signal to be transmitted. The modulating unit may form a signal suitable for a body coupled communication, wherein the signal ideally contains no spectral content in the frequency range of physiological signals to be sensed by the device itself and other devices, such that any interference with these physiological signals is avoided. To improve this, the device can further comprise a third filtering unit configured to high-pass filter a body coupled communication signal to be transmitted. The third filtering unit may be used to suppress signal components in a frequency range of physiological signals to be sensed. Thus, the sensing of physiological signals can be improved, since less interference due to transmitted body coupled communication signals occurs. As a result, a more accurate estimate of a physiological quantity may be obtained.

The device can comprise a communicating unit configured to communicate a communication signal to a device separated from the human or animal body. The communicating unit can be used to deliver data such as e.g. raw or processed physiological data sensed by the device or received thereby to a device separate from the human or animal body. On the one hand, this enables usage of the device as a hub forwarding data originating from other devices. On the other hand, applications such as a remote medical monitoring station used to monitor and display physiological functions of a patient and output an alarm message in case that a critical event arises may be implemented by means of the communicating unit.

The device can be configured to simultaneously sense the physiological signal and communicate the body coupled communication signal. Therefore, the same couplers may be used to continuously sense a physiological signal and communicate a body coupled communication signal, without the need for extra communication means and/or intermittent sensing or communicating.

The device can be configured to simultaneously sense multiple physiological signals. Thus, it is possible to sense different physiological signals, e.g. an ECG signal and an EMG signal measured together at a muscle, by a single device. Hence, it is not necessary to use multiple devices or sensing units for this purpose. As a result, the size, the complexity and the costs of a sensing system for sensing different physiological signals may be reduced.

The device can be integrateable into at least one of textile, shoes and sports equipment. This enables applications in the fields of e.g. wellness and sports with an increased convenience. For example, if physiological functions of an athlete are to be monitored, the athlete only needs to put his/her sportswear on or even just has to utilize sports equipment. Further, it might also be easier, more reliable and more convenient to measure physiological signals of patients in a clinical environment, as the device could simply be integrated e.g. into clothing or a bed of the patient. In both of these cases and for other applications the device does not have to be glued or connected with gel to the person.

The device may be at least one of a capacitive contactless sensor, a body area network sensor and a medical on-body sensor. If the device is e.g. a body area network sensor or a medical on-body sensor, it can easily be interconnected with other sensors of the same type in order to form a sensor network. Thus, no adaptation effort is required.

In a second aspect of the present invention a system comprising a plurality of devices according to the first aspect is presented, wherein at least two devices of the plurality of devices are configured to communicate with each other. With a system of this kind, there is no need for using wires. Thus, no clutter of wires occurs. Further, the system is less complex as compared with a system employing an extra RF communication unit or other kind of communication unit. Hence, it can be low-power and low-cost. The system may potentially even be ultra low-power and low-cost, since it does not require an extra antenna and RF unit.

The system can be at least one of a body area network and a medical on-body sensor network. A system of such type may easily be employed e.g. for medical applications and does not need to be adapted so as to monitor a patient or serve other purposes.

In a third aspect of the present invention a device according to the first aspect is used for patient monitoring, sports performance coaching or wellness applications. When using the device for such applications, no wires or extra communication solutions are needed. Therefore, a more reliable, more convenient and cheaper setup is feasible.

In a fourth aspect of the present invention a method is presented that comprises: a) capacitively sensing a physiological signal from a human or animal body; and b) capacitively communicating a body coupled communication signal for a body area network, wherein the steps a) and b) are performed by a sensing unit of a device being placeable on or close to a human or animal body. The method enables to use a single sensing unit for sensing or measuring a physiological signal and communicating a body coupled communication signal. In other words, the same couplers can simultaneously be used for sensing, transmitting and receiving. Thus, sensing and communicating can be performed at the same time by the same sensing unit. Hence, the size, the costs and the power consumption of a device comprising the sensing unit can be reduced in comparison with those of previously proposed devices. The device may potentially be ultra low-power and low-cost, since it does not require an extra antenna and RF unit. Moreover, there is no need for using wires. Therefore, no clutter of wires occurs.

In a fifth aspect of the present invention a computer program is presented, wherein the computer program comprises program code means for causing a computer to carry out the steps of a method according to the fourth aspect when the computer program is carried out on a computer. Thus, the same advantages as with the method according to the fourth aspect can be achieved.

With the first to fifth aspects of the present invention a communication between devices used to sense physiological signals may be confined to one human or animal body. Further, such communication can be robust and does not require additional hardware, thus showing smaller power consumption and being cheaper than previously proposed solutions. In addition, no body blockage occurs with the communication, since the human or animal body is used as a communication medium.

Further advantageous modifications are defined in the dependent claims.

BRIEF DESCRIPTION OF THE DRAWINGS

These and other aspects of the present invention will be apparent from and elucidated by an embodiment described hereinafter with reference to the accompanying drawings, in which.

DETAILED DESCRIPTION OF AN EMBODIMENT

Figure 1:
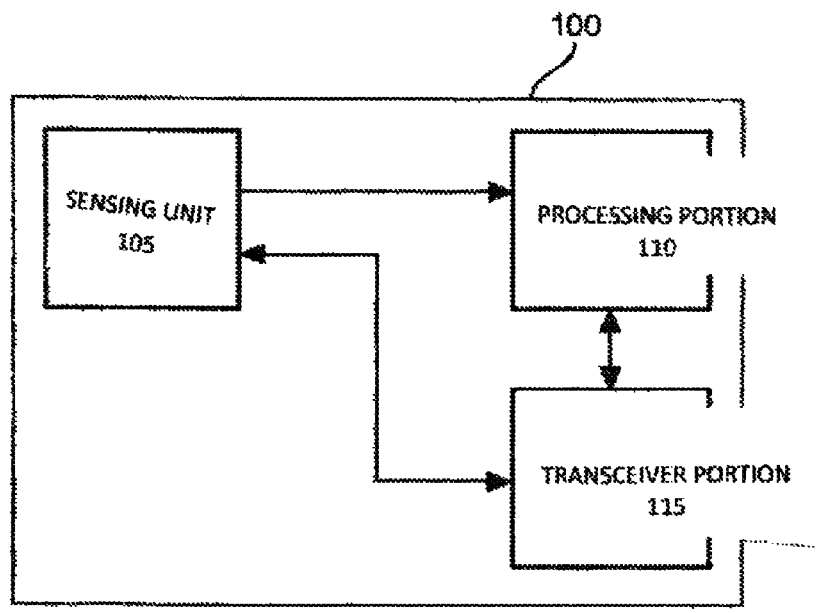
FIG. 1 shows a schematic block diagram illustrating the basic arrangement of an exemplary device according to the embodiment.

FIG. 1 shows a schematic block diagram illustrating the basic arrangement of an exemplary device according to the embodiment. A device 100 comprises a sensing portion or unit 105, a processing portion 110 and a transceiver portion 115. The device 100 can be a sensor or sensor node and is placeable on or close to a human or animal body. A physiological signal may be capacitively sensed or measured by the sensing unit 105. The sensed physiological signal may be supplied from the sensing unit 105 to the processing portion 110. The processing portion 110 can filter and process the sensed physiological signal. Further, it can store a processing result or the unprocessed physiological signal and supply the same to the transceiver portion 115. In addition, a body coupled communication (BCC) signal may be communicated by the sensing unit 105, wherein the human or animal body is used as a communication medium. The BCC signal can be intended for a body area network (BAN). The transceiver portion 115 may filter and detect a received BCC signal picked up by the sensing unit 105. Further, the transceiver portion 115 can generate and filter a BCC signal to be transmitted via the sensing unit 105 and the human or animal body. A transmitted BCC signal may comprise information on sensing results, i.e. measured physiological signals.

Figure 2:
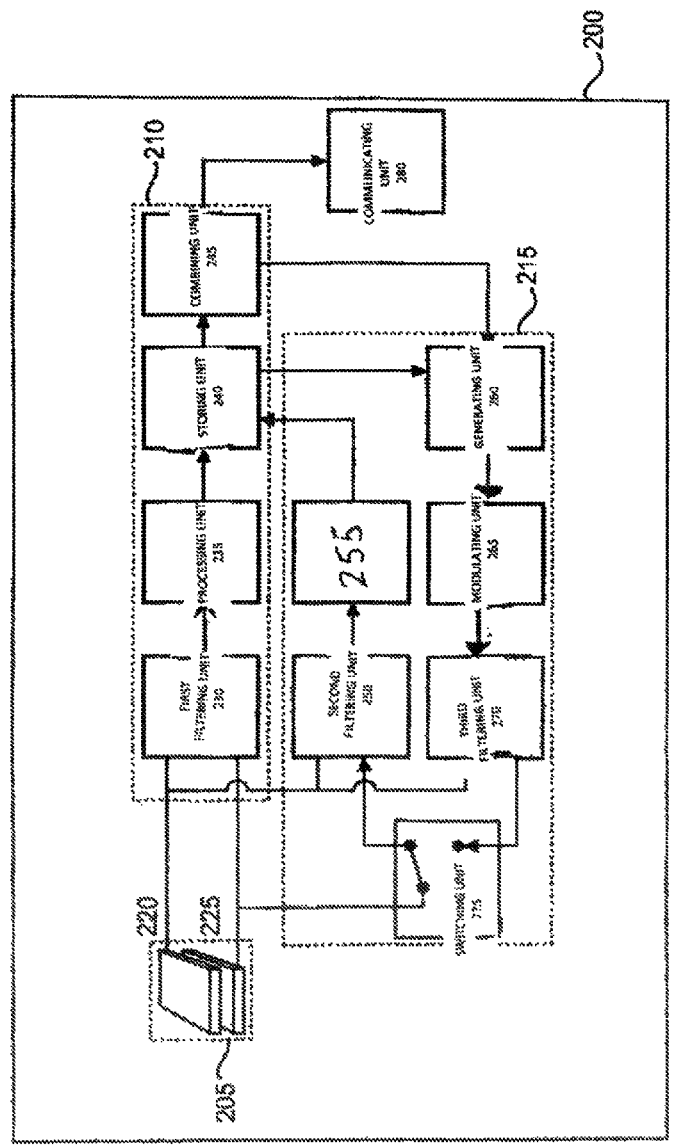
FIG. 2 shows a schematic block diagram illustrating the exemplary device according to the embodiment in more detail.

FIG. 2 shows a schematic block diagram illustrating the exemplary device according to the embodiment in more detail. A device 200 depicted in FIG. 2 corresponds to the device 100 shown in FIG. 1. The device 200 comprises a sensing unit 205, a processing portion 210 and a transceiver portion 215 respectively corresponding to the sensing unit 105, the processing portion 110 and the transceiver portion 115 as shown in FIG. 1. The sensing unit 205 includes two electrodes 220, 225. The electrodes 220, 225 are illustrated as ideal flat plates but may also have other forms. The processing portion 210 comprises a first filter or filtering unit 230, a processing unit 235 such as e.g. a sensor signal processing unit, a storing unit 240 such as e.g. a memory device and a combining unit 245 such as e.g. a data fusion unit. The transceiver portion 215 comprises a second filter or filtering unit 250 and a detecting unit 255 in a receiving path or stage as well as a transmit data generating unit 260, a modulating unit 265 and a third filter or filtering unit 270 in a transmitting path or stage. Further, a switching unit 275 such as e.g. a transistor is contained in the transceiver portion 215.

The sensing unit 205 can sense or measure a physiological signal originating from a human or animal body, by means of the electrodes 220, 225 placed on or close to the human or animal body. A ground (GND) reference may be applied for measurements, by using one of the electrodes 220, 225. However, this is optional. Further, another predefined reference can be used as well. In addition, for some configurations only one electrode may be placed on or close to the human or animal body. In such cases, the ground or other predefined reference can be achieved in another way. For example, a ground plate of a transceiver/sensor printed circuit board (PCB) may be used. Other variants include wired ground.

The sensing unit 205 can be used to measure at least one physiological signal such as e.g. an ECG, EEG and/or EMG signal. Such physiological signals typically comprise a low frequency content. Therefore, they can be low-pass filtered by the first filtering unit 230 in order to remove or suppress other spectral content resulting e.g. from BCC signals transmitted by other devices and either being simultaneously received by the sensing unit 205 or just interfering with the sensed physiological signals. The first filtering unit 230 may either be a low-pass filter (LPF) or a band-pass filter (BPF). A BPF can be used to also remove or suppress direct current (DC) signal contributions.

A signal output by the first filtering unit 230 can be processed by the processing unit 235 in order to extract or retrieve a desired physiological quantity to be sensed. The result of this processing procedure may be stored in the storing unit 240. The storing unit 240 can hold results from previous measurements effected by the device 200, measurement results originating from other (capacitive or non-capacitive) devices or sensors connected to the device 200, and/or measurement results of other (capacitive or non-capacitive) devices received over a BCC link. A data fusion (combining) can be applied by the combining unit 245 in order to combine the different measurement results or measured signals so as to make a decision or derive another and/or more accurate estimate of at least one physiological quantity to be sensed. For example, signals can be combined to remove the influence of motion artefacts, which improves the sensing dramatically and alleviates the main disadvantage of capacitive measurements.

The transmit data generating unit 260 may combine data resulting from a data fusion procedure effected by the combining unit 245 and/or data from the storing unit 240 directly with other data in order to generate transmit data to be transmitted over a capacitive (BCC) link to at least one other device. Transmit data generated by the transmit data generating unit 260 can be modulated by the modulating unit 265 in order to form a BCC signal to be transmitted, i.e. a signal suitable for a BCC transmission. This may include modulating and coding the signal and adding training and synchronization structures to the transmit data. Ideally, a BCC transmit (TX) signal to be transmitted via the BCC link comprises no spectral contents in the frequency range of the physiological signal(s) to be sensed. To further improve this, the third filtering unit 270 can be used to filter the BCC TX signal in order to remove or suppress signal components in the corresponding part of the frequency band, i.e. the frequency range of the physiological signal(s) to be sensed. The third filtering unit 270 may be a high-pass filter (HPF). A signal output by the third filtering unit 270 can be transmitted via the sensing unit 205 and the human or animal body, i.e. the BCC link.

The device 200 may be switched from a transmitting mode as described above to a receiving mode in order to receive BCC signals. Switching from the transmitting mode to the receiving mode and vice versa can be effected by the switching unit 275. In FIG. 2 a setting of the switching unit 275 for the receiving mode is illustrated. That is, there is a signal path from the sensing unit 205 to the receiving stage of the transceiver portion 215. For the transmitting mode the switching unit 275 would be set such that there is a signal path from the transmitting stage of the transceiver portion 215 to the sensing unit 205.

In the receiving mode, a BCC signal can be picked up or received by the sensing unit 205. The received BCC signal may be high-pass filtered by the second filtering unit 250 in order to remove or suppress physiological signal content. The second filtering unit 250 can either be a HPF or a BPF. A BPF can be used to also remove or suppress high frequency noise or interference from e.g. RF signals. The detecting unit 255 can apply a detection of a BCC receive (RX) signal to an output of the second filtering unit 250 to detect or retrieve a BCC RX signal transmitted from another device. Thus, data conveyed by the BCC RX signal can be detected or retrieved by means of a detection procedure performed by the detecting unit 255. The detection procedure may include e.g. an automatic gain control (AGC), synchronization, channel estimation, symbol correlation and decoding. The detected or retrieved data can be stored in the storing unit 240. Subsequently, processing such as the above described data fusion (combining) applied by the combining unit 245 may be applied to it.

The device 200 may comprise a communicating unit 280 such as e.g. a radio frequency (RF) unit or a unit enabling wired connections. In this case it can serve as a hub in a system comprising multiple devices. The communicating unit 280 can comprise elements like a transmit data generating unit, a modulating unit and a filtering unit, similar to the transmitting stage of the transceiver portion 215. It may be configured to communicate a communication signal to a device separated from the human or animal body at which the device 200 is located. The communicating unit 280 can be used to deliver data such as e.g. raw or processed physiological data sensed by the device 200 or received thereby to a device separated from the human or animal body. This enables usage of the device 200 as a hub forwarding data originating from other devices and transmitted to the device 200 via the BCC link. Further, applications such as a remote medical monitoring station used to monitor and display physiological functions of a patient and output an alarm message in case that a critical event arises may be implemented.

The communicating unit 280 can deliver data resulting from a data fusion procedure effected by the combining unit 245 and/or data from the storing unit 240 directly. In this connection, it should be noted that in the exemplary arrangement of FIG. 2 the communicating unit 280 is only connected to the combining unit 245, while it can also be connected to the storing unit 240 in other arrangements.

As an alternative to the above described structure, a time multiplexing of measurements and transmissions, i.e. sensed physiological signals and communicated BCC signals, can be used. That is, two or more devices communicating with each other may be configured to have some common understanding of time. Then, 1 out of x timeslots can be used for sensing, and x−1 out of x timeslots may be used for data transmissions, i.e. communication. Thereby, interference in sensing can be avoided. In other words, a plurality of devices are configured to communicate in a synchronous manner, such that none of the devices communicates during sensing periods.

The device 200 may be integrated into textile, shoes or sports equipment and can be used with a variety of applications. It may be configured to be part of a BAN. In general, the applications of the device 200 are in the field of BANs such as body sensor networks like e.g. medical on-body sensor networks. Its application domain is in both healthcare and lifestyle. Typical applications are in patient monitoring, sports performance coaching and wellness.

Further, the device 200 can be used to simultaneously sense multiple physiological signals. For example, different physiological signals, e.g. an ECG signal and an EMG signal measured together at a muscle, may be simultaneously sensed. It depends on a position of the device 200 at a human or animal body which kinds of physiological signals can be measured together. The simultaneous measurement of different kinds of physiological signals is possible as all these signals have spectral contents in the same frequency range and, therefore, can pass the filtering unit 230 effecting a low-pass filtering. Individual physiological signals can be retrieved by an appropriate processing in the processing unit 235.

Figure 3:
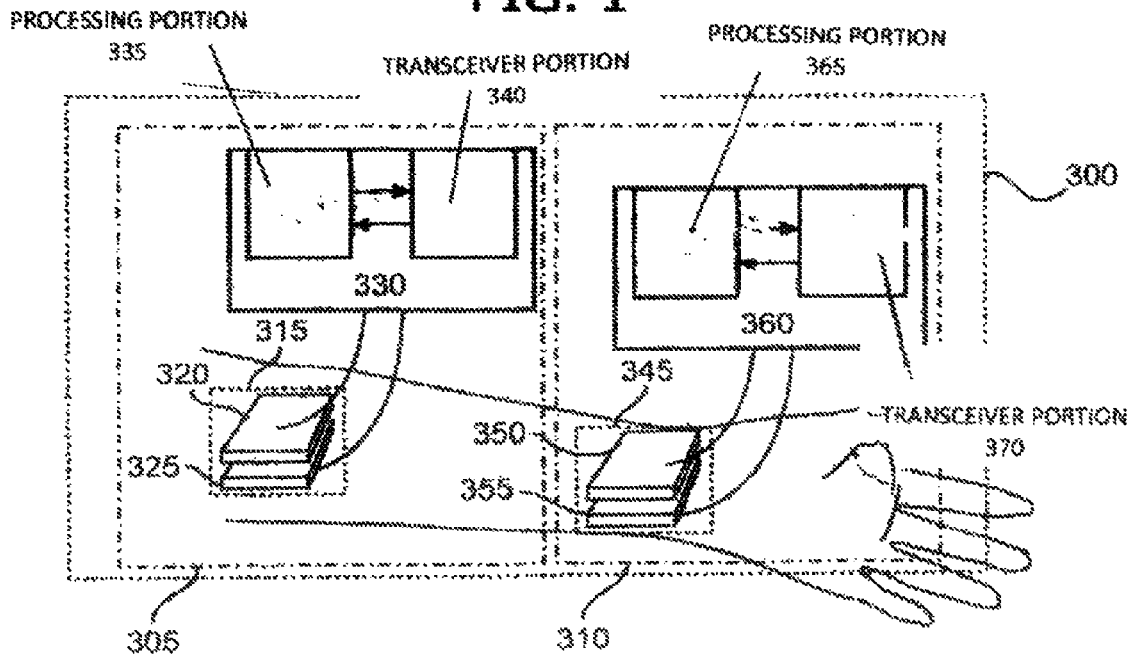
FIG. 3 shows a schematic diagram of an exemplary system comprising two devices according to the embodiment.

FIG. 3 shows a schematic diagram of an exemplary system comprising two devices according to the embodiment. A system 300 depicted in FIG. 3 includes two devices 305, 310 which are placed on or close to a person's forearm. Each of the devices 305, 310 respectively corresponds to the device 100 shown in FIG. 1 and the device 200 shown in FIG. 2. The device 305 comprises a sensing unit 315 including electrodes 320, 325 as well as a sensor node portion 330 including a processing portion 335 and a transceiver portion 340. The device 310 comprises a sensing unit 345 including electrodes 350, 355 as well as a sensor node portion 360 including a processing portion 365 and a transceiver portion 370. The sensing unit 315, processing portion 335 and transceiver portion 340 on the one hand as well as the sensing unit 345, processing portion 365 and transceiver portion 370 on the other hand respectively correspond to the sensing unit 105, processing portion 110 and transceiver portion 115 as shown in FIG. 1 and the sensing unit 205, processing portion 210 and transceiver portion 215 as shown in FIG. 2.

Each of the devices 305, 310 may capacitively sense at least one physiological signal at a portion of the person's forearm where the respective device is placed. Further, the device 305 can capacitively transmit BCC signals conveying data retrieved from at least one sensed physiological signal as well as other data to the device 310 and vice versa. Thus, the devices 305, 310 can exchange such data by means of a BCC communication via a part of the person's forearm extending between the two devices. In other words, the devices 305, 310 are capacitively coupled through this part of the person's forearm.

While only two devices 305, 310 forming a quite small network are depicted in FIG. 3, more than two devices can be used in a larger network such as e.g. a BAN. Further, such devices cannot only be placed on or close to a person's forearm as illustrated in FIG. 3, but may be located at other parts of the person's body. In addition, the application of such devices is not restricted to a human body, but is also possible for an animal body.

Figure 4:
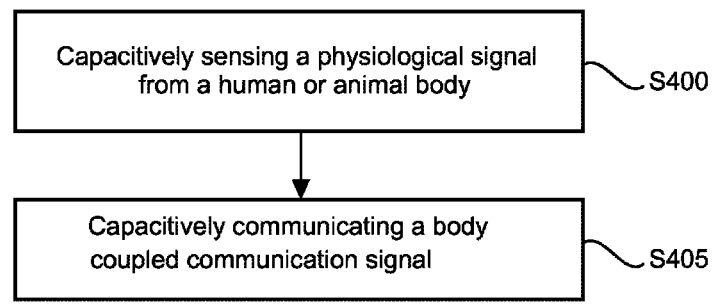
FIG. 4 shows a flowchart illustrating basic steps of an exemplary method according to the embodiment.

FIG. 4 shows a flowchart illustrating basic steps of an exemplary method according to the embodiment. The method comprises a step S400 of capacitively sensing a physiological signal from a human or animal body, and a step S405 of capacitively communicating a BCC signal. Both steps S400 and S405 can be performed by a sensing unit of a device being placeable on or close to a human or animal body. The sensing may comprise measurement and detection of physiological signals. Further, the communication typically comprises transmission and reception of communication signals, wherein these signals may convey information on the content of measured physiological signals. Both of sensing and communication can be performed by a single sensing unit.

Figure 5:
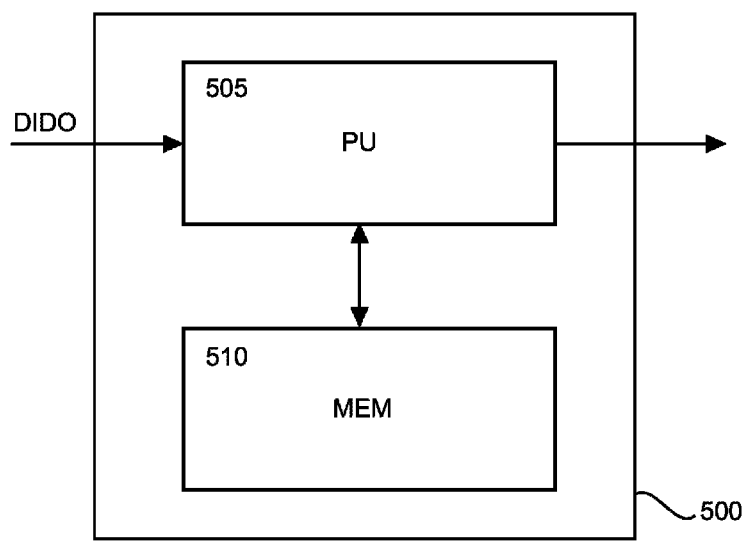
FIG. 5 shows an example of a software-based implementation of the embodiment.

FIG. 5 shows a schematic block diagram of a software-based implementation of the embodiment. Here, a device 500 comprises a processing unit (PU) 505, which may be provided on a single chip or a chip module and which may be any processor or computer device with a control unit that performs control based on software routines of a control program stored in a memory (MEM) 510. Program code instructions are fetched from the MEM 510 and loaded into the control unit of the PU 505 in order to perform the processing steps described in connection with FIG. 4. The processing steps of the blocks S400 and S405 may be performed on the basis of input data DI and may generate output data DO, wherein the input data DI may correspond to data or signals that have been communicated and/or sensed, and the output data DO can correspond to data or signals that are going to be communicated to other devices.

Figure 6:
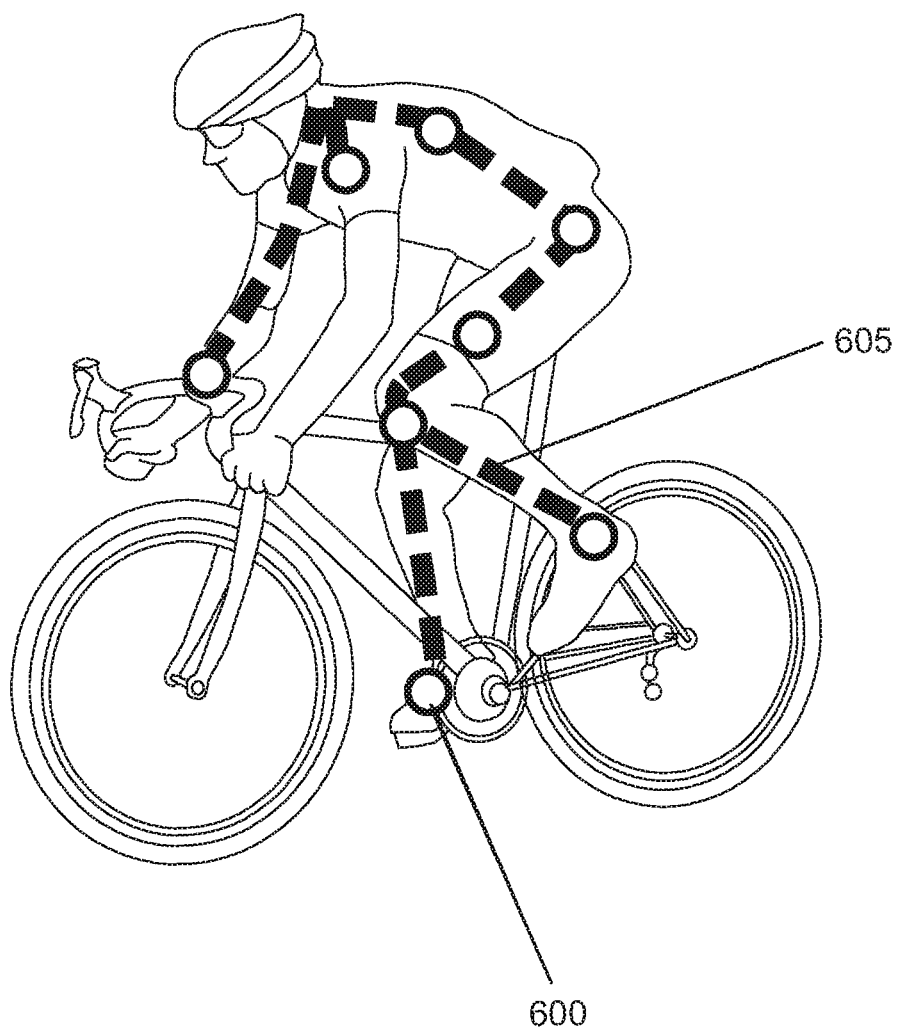
FIG. 6 shows an exemplary application of the embodiment in the field of sports.
Figure 7:
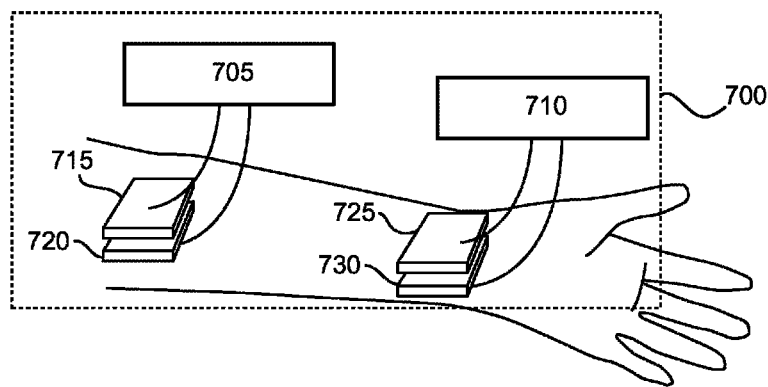
FIG. 7 shows a schematic diagram of a BCC system.
Figure 8:
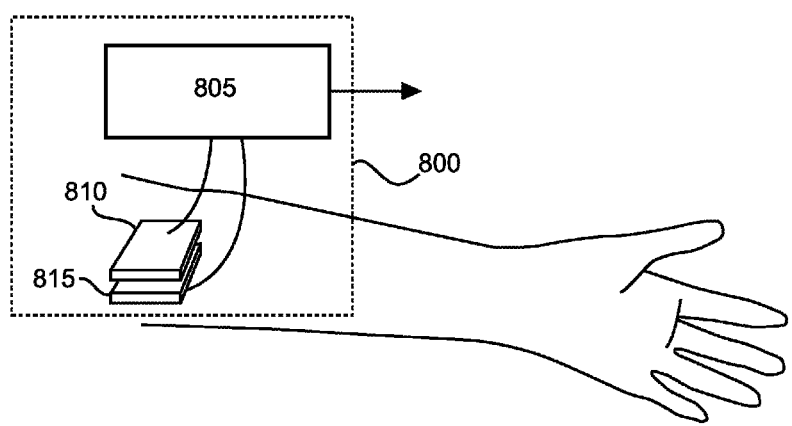
FIG. 8 shows a schematic diagram of a capacitive physiological sensing device.

FIG. 6 shows an exemplary application of the embodiment in the field of sports, with sensor devices 600 integrated in clothes (textile), shoes and sports equipment (here a bike) of an athlete and forming a capacitive body sensor network. A communication path 605 represented by dotted lines in FIG. 6 extends between the sensors 600 represented by dots in FIG. 6. The sensors 600 are preferably placed at the joints of the athlete and at the end of his/her limbs. However, they may also be located at the bike, e.g. at the handle bar or pedals thereof. Each of the sensors respectively corresponds to the devices 100, 200, 305 and 310 as shown in FIGS. 1, 2 and 3.

FIG. 6 illustrates one example of a networked body sensor device that combines a capacitive contactless sensing with BCC to measure human physiological signals and communicate BCC signals that may comprise information on the physiological signal content. As a matter of course, other applications of such device are conceivable. For example, healthcare or medical applications such as e.g. patient monitoring, lifestyle applications such as e.g. wellness, sports performance coaching or other sports applications, military applications, security applications etc. may be implemented by using networked body sensor devices. Further, also animal physiological signals can be measured (sensed), and information on the content of these physiological signals may be communicated by BCC signals.

The present invention uses the same structure for sensing and communicating and may use a human or animal body as a communication medium. A networked body sensor device is proposed as a device which combines BCC, based on capacitive coupling, with a capacitive contactless sensor to measure human or animal physiological signals.

In summary, the invention relates to a device, a method, a system and a computer program, wherein the device is placeable on or close to a human or animal body and comprises at least a sensing unit configured to capacitively sense a physiological signal from the human or animal body and capacitively communicate a body coupled communication signal. As sensing and body coupled communication capabilities can be provided by a single sensing unit, disadvantages of previous solutions for sensing and communicating like e.g. clutter of wires or increased costs and power consumption due to extra communication hardware can be alleviated.

While the present invention has been illustrated and described in detail in the drawings and foregoing description, such illustration and description are to be considered illustrative or exemplary and not restrictive. The invention is not limited to the disclosed embodiments.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor, sensing unit or other unit may fulfil the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope thereof.

The invention claimed is:

1. A device being placeable on or close to a human or animal body, the device comprising:
   a sensing unit configured to capacitively sense a physiological signal during predetermined sensing periods from said human or animal body and to capacitively communicate a body coupled communication signal during predetermined transmission periods,
   a combining unit configured to generate combined data by combining at least one of: data generated by said device at different points in time and data generated by said device and a plurality of other devices, the combining unit being further configured to combine different measured data to decide or derive a further estimate of a physiological quantity,
   a transmit data generating unit configured to generate transmit data from at least one of stored data, said combined data and other data,
   a detecting unit configured to detect data conveyed by a received body coupled communication (BCC) RX signal transmitted from another device,
   wherein said device is configured to communicate in a synchronous manner with said plurality of other devices such that no device communicates with another device during a sensing period by time multiplexing said predetermined measurement periods and said predetermined transmission periods of each device such that a first predetermined number of time slots are allocated to said predetermined sensing periods and a second predetermined number of time slots are allocated to said predetermined transmission periods.

2. The device according to claim 1, further comprising a first filtering unit configured to low-pass filter or band-pass filter said physiological signal.

3. The device according to claim 1, further comprising a processing unit configured to process a signal based on said physiological signal.

4. The device according to claim 1, further comprising a second filtering unit configured to high-pass filter or band-pass filter a received body coupled communication signal.

5. The device according to claim 1, further comprising a storing unit configured to store at least one of data based on said physiological signal, data conveyed by a received body coupled communication signal and data conveyed by another communication signal.

6. The device according to claim 1, further comprising a modulating unit configured to modulate transmit data to obtain a body coupled communication signal to be transmitted.

7. The device according to claim 1, further comprising a third filtering unit configured to high-pass filter a body coupled communication signal to be transmitted.

8. The device according to claim 1, further comprising a communicating unit configured to communicate a communication signal to a device separated from said human or animal body.

9. The device according to claim 1, wherein said device is configured to operate in a non synchronous mode by simultaneously sensing and communicating said physiological signal said body coupled communication signal.

10. The device to claim 1, wherein said device is configured to simultaneously sense multiple physiological signals.

11. The device according to claim 1, wherein said device is integrateable into at least one of textile, shoes and sports equipment.

12. The device according to claim 1, wherein said device is at least one of a capacitive contactless sensor, a body area network sensor and a medical on-body sensor.

13. A system comprising:
   a plurality of devices, wherein each device is placeable on or close to a human or animal body and comprising:
   a sensing unit configured to capacitively sense a physiological signal during predetermined sensing periods from said human or animal body and to capacitively communicate a body coupled communication signal during predetermined transmission periods,
   a combining unit configured to generate combined data by combining at least one of: data generated by said device at different points in time and data generated by said device and a plurality of other devices, the combining unit being further configured to combine different measured data to decide or derive a further estimate of a physiological quantity,
   a transmit data generating unit configured to generate transmit data from at least one of stored data, said combined data and other data,
   a detecting unit configured to detect data conveyed by a received body coupled communication (BCC) RX signal transmitted from another one of said plurality of devices,
   wherein each of said device is configured to communicate in a synchronous manner with said plurality of other devices such that no device communicates during a sensing period by time multiplexing said predetermined measurement periods and said predetermined transmission periods of each device such that a first predetermined number of time slots are allocated to said predetermined sensing periods and a second predetermined number of time slots are allocated to said predetermined transmission periods,
   wherein at least two devices of said plurality of devices are configured to communicate with each other.

14. The system according to claim 13, wherein said system is at least one of a body area network and a medical on-body sensor network.

15. A method comprising:
   a) capacitively sensing a physiological signal during predetermined sensing periods from a human or animal body; and
   b) capacitively communicating a body coupled communication signal during predetermined transmission periods,
   c) detecting data conveyed by a received body coupled communication (BCC) RX signal transmitted from another device,
   d) combine different measured data to decide or derive a further estimate of a physiological quantity, wherein the steps a) and b) are performed by a sensing unit of a device being placeable on or close to a human or animal body wherein step c) is performed by a detecting unit of the device in communication with another device being placeable on or close to a human or animal body.

16. A computer program comprising program code embedded on a tangible, non-transitory computer readable medium, which when loaded into a computer system causes a computer to perform steps including:

a) capacitively sensing a physiological signal during predetermined sensing periods from a human or animal body; and b) capacitively communicating a body coupled communication signal during predetermined transmission periods, c) detecting data conveyed by a received body coupled communication (BCC) RX signal transmitted from another device, d) combine different measured data to decide or derive a further estimate of a physiological quantity, wherein the steps a) and b) are performed by a sensing unit of a device being placeable on or close to a human or animal body wherein step c) is performed by a detecting unit of the device in communication with another device being placeable on or close to a human or animal body.

* * * * *